US008093207B2

(12) United States Patent
Stern

(10) Patent No.: US 8,093,207 B2
(45) Date of Patent: Jan. 10, 2012

(54) FAST-ACTING ORAL PEPTIDE PHARMACEUTICAL PRODUCTS

(75) Inventor: William Stern, Tenafly, NJ (US)

(73) Assignee: Unigene Laboratories, Inc., Boonton, NJ (US)

( * ) Notice: Subject to any disclaimer, the term of this patent is extended or adjusted under 35 U.S.C. 154(b) by 951 days.

(21) Appl. No.: 11/567,454

(22) Filed: Dec. 6, 2006

(65) Prior Publication Data

US 2007/0134279 A1    Jun. 14, 2007

Related U.S. Application Data

(60) Provisional application No. 60/748,954, filed on Dec. 9, 2005.

(51) Int. Cl.
*A61K 38/00* (2006.01)
*A61K 47/12* (2006.01)

(52) U.S. Cl. .......................... 514/1.1; 424/465; 562/584

(58) Field of Classification Search ............... 514/2, 1.1; 424/400, 408, 464, 465; 562/584
See application file for complete search history.

(56) References Cited

U.S. PATENT DOCUMENTS

| 5,204,114 A * | 4/1993 | Demopoulos et al. ......... 424/465 |
| 5,534,496 A * | 7/1996 | Lee et al. ......................... 514/17 |
| 5,958,886 A * | 9/1999 | Carter et al. ..................... 514/19 |
| 6,022,860 A * | 2/2000 | Engel et al. ...................... 514/15 |
| 6,159,500 A * | 12/2000 | Demopoulos et al. ......... 424/456 |
| 6,355,270 B1 * | 3/2002 | Ferrari et al. ................... 424/489 |
| 6,703,483 B1 | 3/2004 | Schiller et al. ................. 530/330 |
| 2005/0214331 A1 * | 9/2005 | Levy .............................. 424/400 |

FOREIGN PATENT DOCUMENTS

| CA | 2 070 061 | 2/2004 |
| WO | WO 97/33531 | 9/1997 |
| WO | WO 00/55189 | 9/2000 |
| WO | WO 02/05748 | 1/2002 |
| WO | WO 02/43767 A1 | 6/2002 |
| WO | WO 02/072075 A1 | 9/2002 |
| WO | WO 2004/064758 A2 | 8/2004 |
| WO | WO 2005/072277 A2 | 8/2005 |
| WO | WO 2006/007332 A1 | 1/2006 |

OTHER PUBLICATIONS

Fix, J.A., Am. J. Physiol. 251:G332-G340 (1986).*
Pirie, N. (J. Biol Chem 84, 321-333, 1929).*
"Buffers", Calbiochem Guide, pp. 1-32, 2003.*
Wan H., Desiderio D.M., "Quantification of [Dmtl]DALDA in ovine plasma by on-line liquid chromatography/quadrupole time-of-flight mass spectrometry", Rapid Commun Mass Spectrom., 17(6):538-46, 2003, abstract, http://www.ncbi.nlm.nih.gov/pubmed/12621615?dopt-Abstract.
Wu D, Soong, Y., Zhao G.M., Zeto H.H., "A highly potent,Peptide analgesic that protects against ischemia-reperfusion-induced myocardial stunning", Am J. Physiol Heart Circ. Physiol, Aug. 2002, 283(2):H783-H791; 10.1152/ajpheart.00193.2002.
U.S. Appl. No. 11/144,580, filed Jun. 2 2005 in the name of Nozer M. Mehta et al. entitled "Oral Delivery of Peptide Pharmaceutical Compositions".
Canadian Office Action dated Feb. 15, 2010 in corresponding Canadian Patent Application No. 2,631,841 (English language).
International Search Rport mailed Nov. 26, 2007 in corresponding International Application No. PCT/US2006/047108.

* cited by examiner

*Primary Examiner* — David Lukton

(74) *Attorney, Agent, or Firm* — Greenberg Traurig, LLP; David J. Dykeman; Danielle T. Abramson

(57) ABSTRACT

A finished pharmaceutical product adapted for oral delivery of a physiologically active peptide agent, wherein the product comprises a therapeutically effective amount of the active peptide agent; at least one pharmaceutically acceptable pH-lowering agent; and at least one absorption enhancer effective to promote bioavailability of the active agent, wherein the pH-lowering agent is present in the finished pharmaceutical product in a quantity which, if the product were added to 10 milliliters of 0.1M aqueous sodium bicarbonate solution, would be sufficient to lower the pH of the solution to no higher than 5.5, and wherein an outer surface of the product is substantially free of an acid-resistant protective vehicle. The product is adapted for use in a method for enhancing the bioavailability of a therapeutic peptide active agent delivered orally.

13 Claims, No Drawings

FAST-ACTING ORAL PEPTIDE PHARMACEUTICAL PRODUCTS

CROSS REFERENCE TO RELATED APPLICATION

This application claims the priority of Provisional Application No. 60/748,954 filed Dec. 9, 2005, the contents of which are specifically incorporated by reference herein.

BACKGROUND OF THE INVENTION

1. Field of the Invention

The present invention relates to oral peptide pharmaceuticals where the active compounds include a plurality of amino acids and at least one peptide bond in their molecular structures, and to methods of quickly providing good bioavailability of such peptide active compounds when administered orally.

2. Description of the Related Art

Numerous human hormones, neurotransmitters and other important biological compounds have peptides as a substantial part of their molecular structures. Many diseases respond positively to raising the level of these peptide compounds in patients. Therapeutically effective amounts of such biologically relevant peptides may be administered to patients in a variety of ways. However, as discussed further below, oral administration, which is the preferred method, is very difficult with this type of active compound.

Salmon calcitonin, for example, is a peptide hormone which decreases uptake of calcium from bone. When used to treat bone-related diseases and calcium disorders (such as osteoporosis, Paget's disease, hypercalcemia of malignancy, and the like), it has the effect of helping maintain bone density. Many types of calcitonin have been isolated (human calcitonin, salmon calcitonin, eel calcitonin, elkatonin, porcine calcitonin, and chicken calcitonin). There is significant structural non-homology among the various calcitonin types. For example, there is only 50% percent identity between the amino acids making up human calcitonin and those making up salmon calcitonin. Notwithstanding the difference in molecular structure, salmon calcitonin may be used in the human treatment of the calcitonin-responsive diseases discussed above.

Peptide pharmaceuticals used in the prior art frequently have been administered by injection or by nasal administration. Insulin is one example of a peptide pharmaceutical frequently administered by injection. However, injection and nasal administration are significantly less convenient, and involve more patient discomfort than, for example, oral administration. Often this inconvenience or discomfort results in substantial patient noncompliance with a treatment regimen. The more preferred oral administration tends to be problematic, however, because peptide active compounds are very susceptible to degradation in the stomach and intestines. Thus, there is a need in the art for more effective and reproducible oral administration of peptide pharmaceuticals like insulin, salmon calcitonin and others discussed in more detail herein.

Proteolytic enzymes of both the stomach and intestines may degrade peptides, rendering them inactive before they can be absorbed into the bloodstream. Any amount of peptide that survives proteolytic degradation by proteases of the stomach (typically having acidic pH optima) is later confronted with proteases of the small intestine and enzymes secreted by the pancreas (typically having neutral to basic pH optima). Specific difficulties arising from the oral administration of a peptide like salmon calcitonin involve the relatively large size of the molecule, and the charge distribution it carries. This may make it more difficult for salmon calcitonin to penetrate the mucus along intestinal walls or to cross the intestinal brush border membrane into the blood. These additional problems may further contribute to limited bioavailability.

Oral dosage forms which at least partially surmount many of the difficulties described above are disclosed and claimed in U.S. Pat. Nos. 5,912,014 and 6,086,918 to Stern et al., issued Jun. 15, 1999 and Jul. 11, 2000, respectively, which are incorporated herein by reference. Both patents describe peptide dosage formulations which target release of the peptide to the intestine and which enhance bioavailability by administering the peptide in an oral dosage formulation which comprises, in addition to the peptide, at least one pharmaceutically acceptable pH-lowering agent and at least one absorption enhancer effective to promote bioavailability of the peptide. The dosage formulation is, moreover, coated with an enteric coating capable of conducting the peptide, the absorption enhancer and the pH-lowering agent through a patient's stomach, while protecting the peptide from degradation by stomach proteases. Thereafter, the coating dissolves and the peptide, absorption enhancer and pH lowering agent are released together into the intestine of the patient.

In certain instances, however, the condition to be treated by the oral peptide would benefit from more rapid remediation than that provided by the relatively slow dissolution of an enteric coating and related release of the active component(s) within the intestine. One particular example of a condition which benefits from such rapid remediation involves the area of pain relief, where the speed with which such relief is achieved is obviously an important, if not critical, factor to a patient. Furthermore, it is not always required that the active peptide agent(s) be transported all of the way through the stomach and into the intestine. That is, in the case of certain peptide agents, including but not limited to various pain-relievers, it may be most efficacious for absorption of the active agent to occur prior to entry of the formulation into the intestine, e.g., as the material passes down the esophagus or when it is within the patient's stomach. Under such circumstances, while oral bioavailability is still a factor to be considered, patients and/or clinicians may be willing to accept a limited reduction in bioavailability if such reduction is balanced by a corresponding increase in the speed of absorption, and thus of action, by the active agent(s) contained within the formulation.

There has thus been a long-felt need for an oral peptide formulation which is capable of more rapid therapeutic action, i.e, in contrast to the formulations described in the '014 and '918 patents discussed above, while still providing a desirable degree of bioavailability.

SUMMARY OF THE INVENTION

It is, accordingly, an object of the present invention to provide a finished pharmaceutical product, as described below, for rapid oral delivery of a physiologically active peptide agent including, but not limited to, parathyroid hormones, the peptide H-Tyrosine-D-Argenine-Phenylalanine-Lysine-NH$_2$ (DALDA) and its derivatives (hereinafter referred to as "DALDA" derivatives) including, but not limited to DMT-DALDA (i.e., H-2,6-dimethyltyrosine-D-Arginine-Phenylalanine-Lysine-NH$_2$), insulin, calcitonin, vasopressin and others discussed herein. As used herein, the terms "finished" and/or "completely finished" are defined to mean that the product is provided in the final form in which it is to be administered.

It is a further object of the invention to provide therapeutic methods for enhancing the speed of delivery of such peptides by treatment with such finished pharmaceutical product(s).

It is a further object of the invention to provide methods of treating bone-related diseases and calcium disorders by administering, for example, calcitonin or one or more anabolic agents, such as parathyroid hormone, orally via administration of the finished pharmaceutical product described herein.

In one aspect, the disease or disorder is treated by administration of a finished pharmaceutical product adapted for oral delivery of a physiologically active peptide agent, wherein the finished product comprises:

(A) a therapeutically effective amount of said active peptide agent;
(B) at least one pharmaceutically acceptable pH-lowering agent; and
(C) at least one absorption enhancer effective to promote bioavailability of said active agent, wherein said pH-lowering agent is present in said finished pharmaceutical product in a quantity which, if said product were added to ten milliliters of 0.1M aqueous sodium bicarbonate solution, would be sufficient to lower the pH of said solution to no higher than 5.5, and wherein an outer surface of the product is substantially free of an acid-resistant protective vehicle.

Preferred peptide active agents include, but are not limited to DALDA, DMT-DALDA, insulin, parathyroid hormones, including truncated hormonal fragments, in either the free acid or amidated form, vasopressin, calcitonins such as salmon calcitonin and others discussed below.

In another aspect, the invention provides a method for enhancing the speed of delivery of a therapeutic peptide active agent delivered orally, which method comprises selectively releasing the peptide active agent, together with at least one pH-lowering agent and at least one absorption enhancer, within a patient's alimentary canal from a finished pharmaceutical product of the type described above which is adapted for delivery of the peptide active agent, wherein an outer surface of the finished pharmaceutical product is substantially free of an acid-resistant protective vehicle, and wherein said pH-lowering agent and other compounds released therewith are released in a quantity which, if added to 10 milliliters of 0.1M aqueous sodium bicarbonate solution, would be sufficient to lower pH of said solution to no higher than 5.5. The lack of an outer, acid-resistant coating on the finished pharmaceutical product is believed to lead to a significant increase in the speed with which the active peptide agent is absorbed into the patient's blood plasma relative to a corresponding enteric-coated pharmaceutical. As used herein, the word, "corresponding", e.g., a corresponding composition, a corresponding pharmaceutical, etc. should be taken to mean, e.g, a composition or pharmaceutical that is exactly identical to one prepared according to the present invention but having an enteric coating, wherein the presently claimed formulation is completely lacking such an enteric coating.

In a further aspect of the invention, the therapeutic peptide active agent, the at least one pH-lowering agent and the at least one absorption enhancer are released from the finished pharmaceutical product more rapidly than from a corresponding pharmaceutical composition comprising an acid resistant protective vehicle (e.g., an enteric coating). In a still further embodiment, a maximum plasma concentration of the peptide active agent is achieved in the patient in 60 minutes or less.

In another aspect, the invention provides a method for enhancing the bioavailability of salmon calcitonin delivered orally via the finished pharmaceutical product described above, which method comprises selectively releasing said salmon calcitonin, together with at least one pH-lowering agent and at least one absorption enhancer, into a patient's alimentary canal following passage of the finished pharmaceutical product through the patient's mouth; wherein the pH-lowering compound is released by said product in an amount which, if the product were added to 10 milliliters of 0.1M aqueous sodium bicarbonate solution, would be sufficient to lower pH of said solution to no higher than 5.5.

In a further aspect of the invention, the salmon calcitonin, the at least one pH-lowering agent and the at least one absorption enhancer are released from the finished pharmaceutical product more rapidly than from a corresponding pharmaceutical composition comprising an acid resistant protective vehicle. In a still further embodiment, a maximum plasma concentration of the salmon calcitonin is achieved in the patient in 60 minutes or less.

The present invention is believed to reduce the likelihood of proteolytic degradation of the peptide active compound. The effect of stomach proteases, which are typically most active at acid pH, may be minimized if not entirely eliminated by administering the finished pharmaceutical product to the patient on an empty stomach, wherein the stomach will contain few such proteases. The peptide is, thereafter, believed to be further protected from proteolytic attack by intestinal or pancreatic proteases, which are typically most active at basic to neutral pH. Significant quantities of acid (with which the peptide active agent is intermixed) are believed to be reduce the activity of neutral to basic-acting proteases in the intestine (e.g. luminal or digestive protease and proteases of the brush border membrane) by lowering pH below the optimal activity range of these intestinal proteases.

Absorption enhancers within the finished pharmaceutical product are used to enhance transport of the peptide agent through intestinal mucous layers, through the brush border membrane and into the blood. The invention is thereby believed to promote the process by which the peptide crosses the intestinal brush border membrane into the blood, while continuing to protect the peptide from proteolytic degradation.

The simultaneous use of absorption enhancers together with a pH lowering compound, in accordance with the invention, provides a surprisingly synergistic effect on bioavailability relative to absorption enhancer alone, or pH lowering compound alone. Compare Table 4 (infra), formulation I (salmon calcitonin alone), Table 3, formulation I (salmon calcitonin and pH-lowering compound) and Table 4, formulation II (salmon calcitonin and absorption enhancer) with Table 4 formulation III (salmon calcitonin, pH-lowering compound, and absorption enhancer).

Other features and advantages of the present invention will become apparent from the following detailed description of the invention.

DETAILED DESCRIPTION OF THE INVENTION

It has surprisingly been found that administering the pharmaceutical formulations of this invention, without an enteric coating, increases the speed of peptide absorption (relative to corresponding enteric-coated pharmaceuticals) without reducing bioavailability below practical levels. While some reduction in bioavailability does occur, this reduction is not expected to preclude effective medical treatment, or to unduly detract from the advantages of greater speed, especially in applications where such speed is particularly advantageous, i.e., in the case of pain relief. The present invention permits more rapid absorption of the active peptide due to the reduction in the time necessary for the vehicle (e.g., a capsule or tablet) to be dissolved and the active ingredients to be released. It also permits such release further upstream in the alimentary canal, e.g., in the esophagus and/or stomach, instead of awaiting passage of the material into the intestine.

In accordance with the invention, patients in need of treatment with peptide active ingredients are provided with the finished pharmaceutical product of the invention, preferably but not necessarily in tablet form of an ordinary size in the pharmaceutical industry, formed of an oral pharmaceutical composition comprising one or more of such peptide active ingredients (at appropriate dosage). The finished pharmaceutical product may additionally be prepared, if desired, in (for example) capsule form. The dosages and frequency of administering the products are discussed in more detail below. Patients who may benefit are any who suffer from disorders that respond favorably to increased levels of a peptide-containing compound. For example, oral salmon calcitonin, in accordance with the invention, may be used to treat patients who suffer from calcium disorders or bone diseases. The invention may be used, for example, to treat osteoporosis, Paget's disease, hypercalcemia of malignancy and the like, with oral calcitonin, preferably salmon calcitonin. Alternately, the peptide active agent may instead comprise a bone anabolic agent such as a parathyroid hormone, whether full-length or truncated, which may be administered in either the free acid or amidated form. A particular embodiment concerns the administration of PTH[1-31]NH$_2$, i.e., a truncated, amidated parathyroid hormone. In addition, analgesic and/or cardiovascular effects may be obtained through the administration of peptides including the so-called DALDA derivatives, such as dmt-DALDA (H-2,6-dimethyltyrosine-D-Arginine-Phenylalanine-Lysine-NH$_2$). DALDA derivatives and other useful peptides are described in detail in application Ser. No. 11/144,580 filed Jun. 2, 2005, which is assigned to the owner of the present application and which is expressly incorporated herein by reference.

Salmon calcitonin is one active ingredient for use in accordance with the invention. For example, it provides a number of advantages over even human calcitonin, even though used as a pharmaceutical agent for human patients. Among the advantages provided by utilizing salmon calcitonin instead of human calcitonin for the treatment of human osteoporosis are increased potency, analgesia and increased half-life. Salmon calcitonin is more effective than natural human calcitonin in treatment, since lower dosages are necessary than with human calcitonin. There is substantial non-homology between salmon and human calcitonin, with only 50% identity in the amino acid sequences of the two calcitonins.

Without intending to be bound by theory, the pharmaceutical composition of which the finished pharmaceutical product of the invention is comprised is believed to overcome a series of different and unrelated natural barriers to bioavailability. Various components of the pharmaceutical compositions act to overcome different barriers by mechanisms appropriate to each, and result in synergistic effects on the bioavailability of a peptide active ingredient. As discussed below, inherent physical and chemical properties of peptides make certain absorption enhancers more effective than others in boosting its bioavailability.

The peptide active compound is contained within a formulation adopted for oral administration. In accordance with the invention, proteolytic degradation of the peptide by stomach proteases (most of which are active in the acid pH range) is preferably reduced due to administration of the formulation to the patient on an empty stomach (although this is not required in order to achieve adequate results), while degradation by intestinal or pancreatic proteases (most of which are active in the neutral to basic pH range) is reduced due to the effect of the pH lowering agent in adjusting the pH of the intestinal environment to sub-optimal levels. Solubility enhancers aid passage of the peptide active agent through the intestinal epithelial barrier.

The pH-lowering agent is believed to lower the local pH (where the active agent has been released) to levels below the optimal range for many intestinal proteases. This decrease in pH reduces the proteolytic activity of the intestinal proteases, thus affording protection to the peptide from potential degradation should the peptide be present within the intestine. The activity of these proteases is diminished by the temporarily acidic environment provided by the invention. It is preferred that sufficient acid be provided that local intestinal pH is lowered temporarily to 5.5 or below, preferably 4.7 or below and more preferably 3.5 or below. The sodium bicarbonate test described below (in the section captioned "the pH-Lowering Agent") is indicative of the required acid amount. Preferably, conditions of reduced pH persist for a time period sufficient to protect the peptide agent from proteolytic degradation until at least some of the peptide agent has had an opportunity to cross into the bloodstream. For salmon calcitonin, experiments have demonstrated $T_{max}$ of 5-15 minutes for blood levels of salmon calcitonin when the active components are injected directly into the duodenum, ilium or colon. The absorption enhancers of the invention synergistically promote peptide absorption into the blood while conditions of reduced proteolytic activity prevail. The mechanism by which the invention is believed to accomplish the goal of enhanced bioavailability is aided by having active components of the finished pharmaceutical product released together as simultaneously as possible.

The absorption enhancer, which may be a solubility enhancer and/or transport enhancer (as described in more detail below), aids transport of the peptide agent from the alimentary canal into the blood, and may promote the process so that it better occurs during the time period of reduced intestinal pH and reduced intestinal proteolytic activity. Many surface active agents may act as both solubility enhancers and transport (uptake) enhancers. Again without intending to be bound by theory, it is believed that enhancing solubility provides (1) a more simultaneous release of the active components of the invention into the aqueous portion of the alimentary tract, (2) better solubility of the peptide in, and transport through, a mucous layer such as that found along the intestinal walls. Once the peptide active ingredient reaches, e.g., the intestinal walls, an uptake enhancer provides better transport through the brush border membrane of the intestine into the blood, via either transcellular or paracellular transport. As discussed in more detail below, many preferred compounds may provide both functions. In those instances, preferred embodiments utilizing both of these functions may do so by adding only one additional compound to the pharmaceutical composition. In other embodiments, separate absorption enhancers may provide the two functions separately.

Each of the preferred ingredients of the finished pharmaceutical product of the invention is separately discussed below. Combinations of multiple pH-lowering agents, or multiple enhancers can be used as well as using just a single pH-lowering agent and/or single enhancer. Some preferred combinations are also discussed below.

Peptide Active Ingredients

Peptide active ingredients which may benefit from oral delivery in accordance with the invention include any therapeutic agent that is physiologically active and has a plurality of amino acids and at least one peptide bond in its molecular structure. The invention, by several mechanisms, suppresses the degradation of the active ingredients by protease that would otherwise tend to cleave one or more of the peptide bonds of the active ingredient. The molecular structure may further include other substituents or modifications. For example, salmon calcitonin, a useful peptide active agent herein, is amidated at its C-terminus. Both man-made and natural peptides can be orally delivered in accordance with the invention.

Peptide active compounds of the invention include, but are not limited to, insulin, vasopressin, calcitonin (including not only salmon calcitonin, but other calcitonins as well). Other examples include, but are not limited to, calcitonin gene-related peptide, parathyroid hormone (full length or truncated, amidated or in the free acid form, further modified or not), luteinizing hormone-releasing factor, erythropoietin, tissue plasminogen activators, human growth hormone, adrenocorticototropin, various interleukins, enkephalin, DALDA derivatives such as dmt-DALDA and the like. Many others are known in the art. It is expected that any pharmaceutical compound having peptide bonds which would be subject to cleavage in the gastrointestinal tract would benefit from oral delivery in accordance with the present invention because of the reduction in such cleavage that is afforded by the present invention.

When salmon calcitonin is used, it preferably comprises from 0.02 to 0.2 percent by weight relative to the total weight of the overall pharmaceutical composition. Salmon calcitonin is commercially available (for example, from BACHEM, Torrance, Calif.). Alternatively, the calcitonin may be synthesized by known methods, some of which are discussed briefly below. Other peptide active agents should be present at higher or lower concentrations depending on desired target blood concentrations for the active compound and its bioavailability in the oral delivery system of the invention (several are reported in Table 6).

Salmon calcitonin precursors may be made by either chemical or recombinant syntheses known in the art. Precursors of other amidated peptide active agents may be made in like manner. Recombinant production is believed significantly more cost effective. Precursors are converted to active salmon calcitonin by amidation reactions that are also known in the art. For example, enzymatic amidation is described in U.S. Pat. No. 4,708,934 and European Patent Publications 0 308 067 and 0 382 403. Recombinant production is preferred for both the precursor and the enzyme that catalyzes the conversion of the precursor to salmon calcitonin. Such recombinant production is discussed in Biotechnology, Vol. 11 (1993) pp. 64-70, which further describes a conversion of a precursor to an amidated product. The recombinant product reported there is identical to natural salmon calcitonin, and to salmon calcitonin produced using solution and solid phase chemical peptide synthesis. During amidation, a keto-acid such as an alpha-keto acid, or salt or ester thereof, wherein the alpha-keto acid has the molecular structure $RC(O)C(O)OH$, and wherein R is selected from the group consisting of aryl, a C1-C4 hydrocarbon moiety, a halogenated or hydroxylated C1-C4 hydrocarbon moiety, and a C1-C4 carboxylic acid, may be used in place of a catalase co-factor. Examples of these keto acids include, but are not limited to, ethyl pyruvate, pyruvic acid and salts thereof, methyl pyruvate, benzoyl formic acid and salts thereof, 2-ketobutyric acid and salts thereof, 3-methyl-2-oxobutanoic acid and salts thereof, and 2-keto glutaric acid and salts thereof.

The production of the preferred recombinant salmon calcitonin (rsCT) may proceed, for example, by producing glycine-extended salmon calcitonin precursor in E. coli as a soluble fusion protein with glutathione-S-transferase. The glycine-extended precursor has a molecular structure that is identical to active salmon calcitonin except at the C-terminal (where salmon calcitonin terminates -pro-$NH_2$, while the precursor terminates -pro-gly. An α-amidating enzyme described in the above publications catalyzes conversion of precursors to salmon calcitonin. That enzyme is preferably recombinantly produced, for example, in Chinese Hamster Ovary (CHO) cells) as described in the Biotechnology article cited above. Other precursors to other amidated peptides may be produced in like manner. Peptides that do not require amidation or other additional functionalities may also be produced in like manner. Other peptide active agents are commercially available or may be produced by techniques known in the art.

The pH-Lowering Agent

The total amount of the pH-lowering compound to be administered with each administration of salmon calcitonin should preferably be an amount which, when released into the intestine for example, is sufficient to lower the local intestinal pH substantially below the pH optima for proteases found there. The quantity required will necessarily vary with several factors including the type of pH-lowering agent used (discussed below) and the equivalents of protons provided by a given pH-lowering agent. In practice, the amount required to provide good bioavailability is an amount which, when the pharmaceutical product of the invention is added to a solution of 10 milliliters of 0.1 M sodium bicarbonate, lowers the pH of that sodium bicarbonate solution to no higher than 5.5, and preferably no higher than 4.7, most preferably no higher than 3.5. Enough acid to lower pH, in the foregoing test, to about 2.8 has been used in some embodiments. Preferably at least 300 milligrams, and more preferably at least 400 milligrams of the pH-lowering agent are used in the pharmaceutical composition of the invention. The foregoing preferences relate to the total combined weight of all pH-lowering agents where two or more of such agents are used in combination. The oral formulation should not include an amount of any base which, when released together with the pH-lowering compound, would prevent the pH of the above-described sodium bicarbonate test from dropping to 5.5 or below.

The pH-lowering agent of the invention may be any pharmaceutically acceptable compound that is not toxic in the gastrointestinal tract and is capable of either delivering hydrogen ions (a traditional acid) or of inducing higher hydrogen ion content from the local environment. It may also be any combination of such compounds. It is preferred that at least one pH-lowering agent used in the invention have a pKa no higher than 4.2, and preferably no higher than 3.0. It is also preferred that the pH lowering agent have a solubility in water of at least 30 grams per 100 milliliters of water at room temperature.

Examples of compounds that induce higher hydrogen ion content include aluminum chloride and zinc chloride. Pharmaceutically acceptable traditional acids include, but are not limited to acid salts of amino acids (e.g. amino acid hydrochlorides) or derivatives thereof Examples of these are acid salts of acetylglutamic acid, alanine, arginine, asparagine, aspartic acid, betaine, carnitine, carnosine, citrulline, creatine, glutamic acid, glycine, histidine, hydroxylysine, hydroxyproline, hypotaurine, isoleucine, leucine, lysine, methylhistidine, norleucine, ornithine, phenylalanine, proline, sarcosine, serine, taurine, threonine, tryptophan, tyrosine and valine.

Other examples of useful pH-lowering compounds include dicarboxylic and tricarboxylic carboxylic acids. Acids such as acetylsalicylic, acetic, ascorbic, citric, fumaric, glucuronic, glutaric, glyceric, glycocolic, glyoxylic, isocitric, isovaleric, lactic, maleic, oxaloacetic, oxalosuccinic, propionic, pyruvic, succinic, tartaric, valeric, and the like have been found useful.

Other useful pH-lowering agents that might not usually be called "acids" in the art, but which may nonetheless be useful in accordance with the invention are phosphate esters (e.g., fructose 1,6 diphosphate, glucose 1,6 diphosphate, phosphoglyceric acid, and diphosphoglyceric acid). CARBOPOL® (Trademark of BF Goodrich) and polymers such as polycarbophil may also be used to lower pH.

Any combination of pH lowering agent that achieves the required pH level of no higher than 5.5 in the sodium bicarbonate test discussed above may be used. One preferred embodiment utilizes, as at least one of the pH-lowering agents in the finished pharmaceutical product, an acid selected from the group consisting of citric acid, tartaric acid and an acid salt of an amino acid.

When salmon calcitonin is the peptide active agent, certain ratios of pH-lowering agent to salmon calcitonin have proven especially effective. It is preferred that the weight ratio of pH-lowering agent to salmon calcitonin exceed 200:1, preferably 800:1 and most preferably 2000:1.

The Absorption Enhancer

The absorption enhancers are preferably present in a quantity that constitutes from 0.1 to 20.0 percent by weight, relative to the overall weight of the pharmaceutical composition. Preferred absorption enhancers are surface active agents which act both as solubility enhancers and uptake enhancers. Generically speaking, "solubility enhancers" improve the ability of the components of the invention to be solubilized in either the aqueous environment into which they are originally released or into, for example, the lipophilic environment of the mucous layer lining the intestinal walls, or both. "Transport (uptake) enhancers" (which are frequently the same surface active agents used as solubility enhancers) are those which facilitate the ease by which peptide agents cross the intestinal wall.

One or more absorption enhancers may perform one function only (e.g., solubility), or one or more absorption enhancers may perform the other function only (e.g., uptake), within the scope of the invention. It is also possible to have a mixture of several compounds some of which provide improved solubility, some of which provide improved uptake and/or some of which perform both. Without intending to be bound by theory, it is believed that uptake enhancers may act by (1) increasing disorder of the hydrophobic region of the membrane exterior of cells, allowing for increased transcellular transport; or (2) leaching membrane proteins resulting in increased transcellular transport; or (3) widening pore radius between cells for increased paracellular transport.

Surface active agents are believed to be useful both as solubility enhancers and as uptake enhancers. For example, detergents are useful in (1) solubilizing all of the active components quickly into the aqueous environment where they are originally released, (2) enhancing lipophilicity of the components of the invention, especially the peptide active agent, aiding its passage into and through the intestinal mucus, (3) enhancing the ability of the normally polar peptide active agent to cross the epithelial barrier of the brush border membrane; and (4) increasing transcellular or paracellular transport as described above.

When surface active agents are used as the absorption enhancers, it is preferred that they be free flowing powders for facilitating the mixing and loading of capsules during the manufacturing process. Because of inherent characteristics of salmon calcitonin and other peptides (e.g., their isoelectric point, molecular weight, amino acid composition, etc.) certain surface active agents interact best with certain peptides. Indeed, some can undesirably interact with the charged portions of salmon calcitonin and prevent its absorption, thus undesirably resulting in decreased bioavailability. It is preferred, when trying to increase the bioavailability of salmon calcitonin or other peptides that any surface active agent used as an absorption enhancer be selected from the group consisting of (i) anionic surface active agents that are cholesterol derivatives (e.g., bile acids), (ii) cationic surface agents (e.g., acyl carnitines, phospholipids and the like), (iii) non-ionic surface active agents, and (iv) mixtures of anionic surface active agents (especially those having linear hydrocarbon regions) together with negative charge neutralizers. Negative charge neutralizers include but are not limited to acyl carnitines, cetyl pyridinium chloride, and the like. It is also preferred that the absorption enhancer be soluble at acid pH, particularly in the 3.0 to 5.0 range.

One especially preferred combination that has worked well with salmon calcitonin mixes cationic surface active agents with anionic surface active agents that are cholesterol derivatives, both of which are soluble at acid pH.

A particularly preferred combination is an acid soluble bile acid together with a cationic surface active agent. An acyl carnitine and sucrose ester is a good combination. When a particular absorption enhancer is used alone, it is preferred that it be a cationic surface active agent. Acyl carnitines (e.g., lauroyl carnitine), phospholipids and bile acids are particularly good absorption enhancers, especially acyl carnitine. Anionic surfactants that are cholesterol derivatives are also used in some embodiments. It is the intent of these preferences to avoid interactions with the peptide agent that interfere with absorption of peptide agent into the blood.

To reduce the likelihood of side effects, preferred detergents, when used as the absorption enhancers of the invention, are either biodegradable or reabsorbable (e.g. biologically recyclable compounds such as bile acids, phospholipids, and/or acyl carnitines), preferably biodegradable. Acylcarnitines are believed particularly useful in enhancing paracellular transport. When a bile acid (or another anionic detergent lacking linear hydrocarbons) is used in combination with a cationic detergent, salmon calcitonin is better transported both to and through the intestinal wall.

Preferred absorption enhancers include: (a) salicylates such as sodium salicylate, 3-methoxysalicylate, 5-methoxysalicylate and homovanilate; (b) bile acids such as taurocholic, tauorodeoxycholic, deoxycholic, cholic, glycholic, lithocholate, chenodeoxycholic, ursodeoxycholic, ursocholic, dehydrocholic, fusidic, etc.; (c) non-ionic surfactants such as polyoxyethylene ethers (e.g. Brij 36T, Brij 52, Brij 56, Brij 76, Brij 96, Texaphor A6, Texaphor A14, Texaphor A60 etc.), p-t-octyl phenol polyoxyethylenes (Triton X-45, Triton X-100, Triton X-114, Triton X-305 etc.) nonylphenoxypoloxyethylenes (e.g. Igepal CO series), polyoxyethylene sorbitan esters (e.g. Tween-20, Tween-80 etc.); (d) anionic surfactants such as dioctyl sodium sulfosuccinate; (e) lyso-phospholipids such as lysolecithin and lysophosphatidyletha-nolamine; (f) acylcarnitines, acylcholines and acyl amino acids such as lauroylcarnitine, myristoylcarnitine, palmitoyl-carnitine, lauroylcholine, myristoylcholine, palmitoylcholine, hexadecyllysine, N-acylphenylalanine, N-acylglycine etc.; g) water soluble phospholipids such as diheptanoylphosphatidylcholine, dioctylphosphatidylcholine etc.; (h) medium-chain glycerides which are mixtures of mono-, di- and triglycerides containing medium-chain-length fatty acids (caprylic, capric and lauric acids); (i) ethylene-diaminetetraacetic acid; (j) cationic surfactants such as cetylpyridinium chloride; (k) fatty acid derivatives of polyethylene glycol such as Labrasol, Labrafac, etc.; and (l) alkylsaccharides such as lauryl maltoside, lauroyl sucrose, myristoyl sucrose, palmitoyl sucrose, etc.

In some preferred embodiments, and without intending to be bound by theory, cationic ion exchange agents (e.g. detergents) are included to provide solubility enhancement by another possible mechanism. In particular, they may prevent the binding of salmon calcitonin or other peptide active agents to mucus. Preferred cationic ion exchange agents include protamine chloride or any other polycation.

Other Optional Ingredients

In some preferred embodiments, another peptide (such as albumin, casein, soy protein, other animal or vegetable proteins and the like) is included to reduce non-specific adsorption (e.g., binding of peptide to the intestinal mucus barrier) thereby lowering the necessary concentration of the expensive peptide active agent. When added, the peptide is preferably from 1.0 to 10.0 percent by weight relative to the weight of the overall pharmaceutical composition. Preferably, this second peptide is not physiologically active and is most preferably a food peptide such as soy bean peptide or the like. Without intending to be bound by theory, this second peptide may also increase bioavailability by acting as a protease scavenger that desirably competes with the peptide active agent for protease interaction. The second peptide may also aid the active compound's passage through the liver.

All pharmaceutical compositions of the invention may optionally also include common pharmaceutical diluents, glycants, lubricants, gelatin capsules, preservatives, colorants and the like in their usual known sizes and amounts.

Other Preferences

It is preferred that the weight ratio of pH-lowering agent(s) to absorption enhancer(s) be between 3:1 and 20:1, preferably 4:1-12:1, and most preferably 5:1-10:1. The total weight of all pH-lowering agents and the total weight of all absorption enhancers in a given pharmaceutical composition is included in the foregoing preferred ratios. For example, if a pharmaceutical composition includes two pH-lowering agents and three absorption enhancers, the foregoing ratios will be computed on the total combined weight of both pH-lowering agents and the total combined weight of all three absorption enhancers.

It is preferred that the pH-lowering agent, the peptide active agent and the absorption enhancer (whether single compounds or a plurality of compounds in each category) be uniformly dispersed in the finished pharmaceutical product. In one embodiment, the finished pharmaceutical product may be produced in the form of a laminate having two or more layers, wherein the peptide active agent is contained within a first layer and the pH-lowering agent and absorption enhancer are contained within a second layer laminated with said first layer. In another embodiment, the composition of the product comprises granules that include a pharmaceutical binder having the peptide active agent, the pH-lowering agent and the absorption enhancer uniformly dispersed within the binder. Preferred granules may also consist of an acid core, surrounded by a uniform layer of organic acid, a layer of enhancer and a layer of peptide that is surrounded by an outer layer of organic acid. Granules may be prepared from an aqueous mixture consisting of pharmaceutical binders such as polyvinyl pyrrolidone or hydroxypropyl methylcellulose, together with the pH-lowering agents, absorption enhancers and peptide active agents used in the invention.

Manufacturing Process

The dosage form of the present invention comprises, in a preferred embodiment, a tablet comprising a lamination of at least two layers. As used herein, the term "lamination" shall have its conventional meaning as something which is composed of layers of firmly united material, but which involves little, if any, interaction between the layers. The primary component of the first layer is typically the pH-lowering agent described above. The primary components of the second layer are typically the peptide and the absorption enhancer. When combined in the manner described below, the constituents form a tablet having at least two layers. The layers may lie adjacent one another, e.g., the first layer on the top of the finished pharmaceutical product with the second layer being on the bottom or alternately, the first layer may lie within and thereby be encompassed by, the second layer. Although a two layer tablet is preferred due to its relative ease of manufacture, it is also possible to have three or more layers wherein the second layer is substantially comprised of the peptide and the third layer comprises the surfactant.

The first layer is manufactured by granulating at least one pH-lowering agent to form a first layer material. While citric acid is the preferred pH-lowering agent, citric acid alone does not exhibit the required compressibility characteristics. Therefore, during and after the granulation, other materials may be added to the pH-lowering agent to improve its mechanical properties. Specifically, during granulation in a fluidized bed, filler materials such as microcrystalline cellulose and a povidone binder may be added in amounts well known in the art. Next, the resultant granulation is dried and optionally sized in a mill in any manner well understood to those of ordinary skill in the art. Additionally, the granulation may be combined with glidants and lubricants such as talc and magnesium stearate, as described above, to farther improve compressibility and flowability of the granulation, thereby forming the first layer material.

The second layer material is formed by combining a peptide and at least one absorption enhancer (i.e, a surfactant). The second layer also may be manufactured in a fluidized bed. Because the peptide exhibits relatively high biological activity in small quantities, the second layer is produced by spraying the peptide and a binding agent, such as povidone, upon a surfactant or a mixture of at least one excipient and the surfactant. As described above, the surfactant is typically an acyl-carnitine, with lauroyl 1-carnitine preferred in the present invention. The optional excipient typically comprises an amount of a filler, such as microcrystalline cellulose, sufficient to provide proper adhesion between the layers, as understood by one of ordinary skill in the art. The resultant granulation is then dried and optionally sized in a mill in any manner well understood to those of ordinary skill in the art. Finally, the granulation is optionally transferred to a blender where the granulation is optionally blended with a disintegrant such as croscarmellose sodium or one or more other suitable disintegrants in amounts up to about 10.0% of the weight of the granulation, with about 2.0% by weight preferred. Although optional, disintegrants are preferred because they are believed to enhance bioavailability of the peptide by facilitating more complete release of the peptide near the same time as the release of the pH-lowering agent.

Other lubricants and additives such as magnesium stearate and stearic acid as well as other excipients such as colloidal silicon dioxide and povidone may also be added to improve the properties of the second layer material in a manner known in the art.

Next, a portion of the first layer material is fed to a standard two-layer tableting press and filled into a die or mold. The first layer material is then partially compressed to create a first layer. The partial compression is typically necessary to prevent substantial mixing between the first layer material and the second layer material when the second layer material is added to the die. Subsequent to partial compression of the first layer material, the second layer material is then added to the die containing the first layer. The first and second layer materials are then compressed together to form a tablet having two layers.

Typically, the first layer material constitutes about 50% to 90% of the total weight of the final tablet. Preferably, the first layer material constitutes about 70% of the total weight of the tablet. The second layer material typically constitutes about 50% to 10% of the total weight of the final tablet. Preferably, the second layer material comprises about 30% of the total weight of the final tablet.

Since the first layer material had been previously partially compressed into a layer, substantial mixing of the second layer material with the first layer material is avoided. The two layer structure of the present invention substantially prevents contact between the pH-lowering agent and the peptide and surfactant. Specifically, at the interface between the two layers, typically less than 0.1% of the peptide contacts the pH-lowering agent.

In an alternate embodiment, the finished pharmaceutical product of the invention (e.g., salmon calcitonin) may include a size 00 gelatin capsule filled with 0.25 mg. of peptide, 400 mg. of granular citric acid (available, for example, from Archer Daniels Midland Corp.), 50 mg. of taurodeoxycholic acid (available, for example, from SIGMA) and 50 mg. lauroyl carnitine (SIGMA). All of the ingredients are preferably adapted for eventual insertion into the gelatin capsule, and are preferably powders which may be added to a blender in any order. Thereafter, the blender is run for about 5 minutes until the powders are thoroughly intermixed. Then the mixed powders are loaded into the large end of the gelatin capsules. The other end of the capsule is then added, and the capsules are snapped shut.

Because of the enhanced bioavailability provided by the present invention, the concentration of the relatively expensive peptide active agent (e.g., salmon calcitonin, PTH, Vasopressin, DALDA, DMT-DALDA, insulin, etc.) in the pharmaceutical preparation of the invention may be kept relatively low. Specific formulation examples are set forth in the examples provided infra.

Treatment of Patients

When salmon calcitonin is chosen as active ingredient for treatment of osteoporosis, periodic administration is recommended. Salmon calcitonin is metabolized quickly with a half-life of only 20-40 minutes following subcutaneous administration in man. However, its beneficial effect on osteoclasts is much longer lasting, and may last for more than 24 hours notwithstanding rapid decrease in blood levels. There is usually no detectable blood levels more than two hours after injection of salmon calcitonin at conventional dosages. Accordingly, periodic administration of one dose about 5 days per week is preferred. Subcutaneous administration of salmon calcitonin (100 International units) has frequently resulted in peak serum concentration of about 250 picograms per milliliter. Nasally administered salmon calcitonin (200 International units) has proven effective against osteoporosis at peak levels as low as 10 picograms per milliliter. Some patients report some gastrointestinal distress at high peak levels (e.g. at or above 200 picograms per milliliter). Accordingly, it is preferred that serum salmon calcitonin peak between 10 and 150 picograms per milliliter, more preferably between 10 and 50 picograms per milliliter. The serum levels may be measured by radioimmunoassay techniques known in the art. The attending physician may monitor patient response, salmon calcitonin blood levels, or surrogate markers of bone disease (such as urinary pyridinoline or deoxypyridinoline), especially during the initial phase of treatment (1-6 months). He may then alter the dosage somewhat to account for individual patient metabolism and response.

The bioavailability achievable in accordance with the present invention permits oral delivery of salmon calcitonin into the blood at the above-identified preferred concentration levels while using only 300-3000 micrograms of salmon calcitonin per capsule, preferably 300-1,200 micrograms, especially between 300 and 600 micrograms.

It is preferred that a single tablet or capsule be used at each administration because a single dose of the product best provides simultaneous release of the polypeptide, pH-lowering agent and absorption enhancers. This is highly desirable because the acid is best able to reduce undesirable proteolytic attack on the polypeptide when the acid is released in close time proximity to release of the polypeptide. Near simultaneous release is thus best achieved by administering all components of the invention as a single tablet or capsule. However, the invention also includes, for example, dividing the required amount of acid and enhancers among two or more tablets or capsules which may be administered together such that they together provide the necessary amount of all ingredients. The term "Pharmaceutical composition," as used herein includes a complete dosage appropriate to a particular administration to a human patient regardless of how it is subdivided so long as it is for substantially simultaneous administration.

Set forth below are a series of tables showing the effect on bioavailability caused by varying certain parameters. Except with regard to human studies reported here, ingredient amounts may be varied from those claimed herein to account for differences between humans and the animals used in the animal models.

TABLE 1

Effect of Buffer pH on the Absorption of Salmon Calcitonin from the Duodenum of the Rat

| | Formulation | pH* | Peak Plasma Calcitonin ng/ml | Absolute Bioavailability Percent |
|---|---|---|---|---|
| I. | Citrate/Citric acid (77 mg) Calcitonin (0.1 mg) | 5 | 0.4 | 0.02 |
| II. | Citrate/Citric acid (77 mg) Calcitonin (0.1 mg) | 4 | 1.9 | 0.10 |
| III. | Citrate/Citric acid (77 mg) Calcitonin (0.1 mg) | 3 | 4.1 | 0.64 |
| IV. | Citrate/Citric acid (77 mg) Calcitonin (0.1 mg) | 2 | 4.8 | 0.69 |

*buffer pH

Method:

Female Wistar rats (250-275 g) (n=3 for each formulation) were anesthetized with ketamine and xylazine prior to the insertion of a cannula in the carotid artery. The cannula was fitted to a three way valve through which blood was sampled and replaced with physiological saline. A midline incision was made in the abdominal cavity and 0.5 ml of formulation was injected directly into the exposed duodenum. The pH of the formulation was adjusted by mixing varying amounts of equal molar concentrations of citric acid and sodium citrate. Blood (0.5 ml) was collected before and at 5, 15, 30, 60 and 120 minutes after the administration of the formulation. Samples of blood were centrifuged for 10 minutes at 2600 g and the resulting plasma supernatant was stored at −20° C. The concentration of calcitonin in plasma was determined by a competitive radioimmunoassay. The absolute bioavailability (i.e., relative to an intravenous dose of calcitonin) was calculated from the areas under the curve obtained from plots of the plasma concentration of calcitonin as a function of time.

Results and Discussion:

When the pH of the buffer was reduced from 5 (formulation I) to 4 (formulation II) the absolute bioavailability increased 5 fold from 0.02% to 0.1%. When the pH was reduced to 3 (formulation III) the absolute bioavailability increased an additional 6.4 fold. There was very little increase in the bioavailability of calcitonin when the pH was reduced to 2. The overall bioavailability of calcitonin increased 32 fold when the pH of the buffer was reduced from 5 to 3.

TABLE 2

Effect of Citric Acid Concentration on the Bioavailability of Salmon Calcitonin from the Duodenum of the Rat

| | Formulation | Peak Plasma Calcitonin ng/ml | Absolute Bioavailability Percent |
|---|---|---|---|
| I. | Citric acid (9.6 mg) Taurodeoxycholic acid (5 mg) Mannitol (22 mg) Calcitonin (0.1 mg) | 3.65 | 0.25 |
| II. | Citric acid (48 mg) Taurodeoxycholic acid (5 mg) Mannitol (22 mg) Calcitonin (0.1 mg) | 17.44 | 2.43 |

Method:

Formulations consisting of a constant amount of taurodeoxycholic acid and 2 different amounts of citric acid in a total volume of 0.5 ml were administered into the duodenums of anesthetized rats as described in the legend to Table 1. Mannitol was included in formulations as a marker to measure paracellular transport. Samples of blood were removed at various times and analyzed for calcitonin as described previously.

Results and Discussion:

The bioavailability of salmon calcitonin administered in the presence of 9.6 mg citric acid (I) was 0.25%, whereas in the presence of 48 mg citric acid (II) the bioavailability was 2.43%. In the presence of a fixed amount of taurodeoxycholic acid the bioavailability of salmon calcitonin increased nearly 10 fold when the amount of citric acid in the formulation was increased only 5 fold.

TABLE 3

Effect of Enhancers in the Presence of Citric Acid on the Absorption of Salmon Calcitonin from the Duodenum of the Rat

| | Formulation | Peak Plasma Calcitonin ng/ml | Absolute Bioavailability Percent |
|---|---|---|---|
| I. | Citric acid (77 mg) Calcitonin (0.1 mg) | 4.8 | 0.69 |
| II. | Citric acid (48 mg) Taurodeoxycholic acid (5 mg) Calcitonin (0.1 mg) | 26.59 | 3.03 |
| III. | Citric Acid (48 mg) Taurodeoxycholic acid (5 mg) Cetylpyridinium chloride (5 mg) Calcitonin (0.1 mg) | 36.48 | 4.54 |
| IV. | Citric Acid (48 mg) Tween-20 (5 mg) Calcitonin (0.1 mg) | 15.50 | 3.10 |
| V. | Citric Acid (48 mg) Sucrose ester-15 (5 mg) Mannitol (22 mg) Calcitonin (0.1 mg) | 38.93 | 5.83 |
| VI. | Citric Acid (48 mg) Lauroylcarnitine chloride (5 mg) Calcitonin (0.1 mg) | 38.89 | 4.53 |
| VII. | Citric Acid (48 mg) Diheptanoylphosphatidylcholine (5 mg) Calcitonin (0.1 mg) | 20.93 | 2.97 |

Method:

Formulations consisting of citric acid, calcitonin and various classes of enhancers in a total volume of 0.5 ml were administered into the duodenums of anesthetized rats as described in the legend to Table 1. Mannitol was included in formulation V as a marker to measure paracellular transport. Samples of blood were removed at various times and analyzed for calcitonin as described previously.

Results and Discussion:

In the absence of an enhancer, the absolute bioavailability of calcitonin was 0.69%. The inclusion of a water soluble phospholipid (formulation VII) increased the bioavailability 4.3 fold to 2.97%. The most effective enhancer was the sugar ester class (formulation V) in which the calcitonin bioavailability was 5.83%. The use of a mixture of bile acid and a cationic detergent (formulation III), a non-ionic detergent (formulation IV) and an acylcarnitine (formulation VI) resulted in intermediate bioavailabilities ranging from 3.03% to 4.53%. The differences in the bioavailabilities of calcitonin in the presence of various classes of enhancers are minor compared to that observed when only citric acid and no enhancer is present in the formulation.

TABLE 4

Effect of Lauroylcarnitine in the Presence of Various Additives on the Absorption of Salmon Calcitonin from the Duodenum of the Rat

| | Formulation | Peak Plasma Calcitonin ng/ml | Absolute Bioavailability Percent |
|---|---|---|---|
| I. | Calcitonin (1 mg) | 9.44 | 0.096 |
| II. | Lauroylcarnitine chloride (5 mg) Calcitonin (0.1 mg) | 2.27 | 0.17 |
| III. | Lauroylcarnitine chloride (5 mg) Citric Acid (48 mg) Calcitonin (0.1 mg) | 38.89 | 4.53 |
| IV. | Lauroylcarnitine chloride (1 mg) Citric Acid (48 mg) Calcitonin (0.1 mg) | 27.72 | 4.81 |
| V. | Lauroylcarnitine chloride (5 mg) Diheptanoylphosphatidylcholine (5 mg) | 44.89 | 6.45 |

TABLE 4-continued

Effect of Lauroylcarnitine in the Presence of
Various Additives on the Absorption of Salmon
Calcitonin from the Duodenum of the Rat

| | Formulation | Peak Plasma Calcitonin ng/ml | Absolute Bioavailability Percent |
|---|---|---|---|
| VI. | Citric Acid (48 mg) Calcitonin (0.1 mg) Lauroylcarnitine chloride (5 mg) Bovine Serum Albumin (25 mg) Calcitonin (0.1 mg) | 4.58 | 0.42 |

Method:

Formulations consisting of lauroylcarnitine, calcitonin and various other compounds in a total volume of 0.5 ml were administered into the duodenums of anesthetized rats as described in the legend to Table 1. Samples of blood were removed at various times and analyzed for calcitonin as described previously.

Results and Discussion:

In the absence of citric acid or any enhancer (formulation I), the absolute bioavailability of calcitonin was 0.096%. In the presence of 5 mg lauroylcarnitine chloride (formulation II), the bioavailability increased 1.8 fold to 0.17%. When citric acid was included with lauroylcarnitine (formulation III), the bioavailability increased an additional 27 fold to 4.53%. A 5 fold reduction in the amount of lauroylcarnitine but not citric acid (formulation IV), did not significantly reduce the bioavailability of salmon calcitonin. The inclusion of 5 mg diheptanoylphosphatidylcholine to formulation III to produce formulation V increased the bioavailability slightly (1.4 fold). The substitution of 25 mg bovine serum albumin for citric acid (formulation VI) reduced the bioavailability from 4.53% (formulation III) to 0.42%. These results taken together show the synergistic effect between a pH-lowering substance like citric acid and an enhancer like lauroylcarnitine.

TABLE 5

Effect of Formulation on the Absorption of Salmon
Calcitonin from the Duodenum of the Dog

| | Formulation | Peak Plasma Calcitonin ng/ml | Absolute Bioavailability Percent |
|---|---|---|---|
| I. | Calcitonin (25 mg) | 1.15 | 0.015 |
| II. | Citric Acid (192 mg) Calcitonin (10 mg) | 10.65 | 0.37 |
| III. | Citric Acid (192 mg) Taurodeoxycholic acid (20 mg) Calcitonin (5 mg) | 14.99 | 0.81 |

Method:

Modified vascular access ports were surgically implanted into the duodenum, ileum and colon of male beagle dogs. The septum/reservoir bodies of the ports were implanted under the skin and were used as sites for the administration of calcitonin formulations. Before and after the administration of calcitonin formulations into conscious dogs, the ports were flushed with 2 ml of the formulation without calcitonin. Blood (2 ml) was collected through angiocatheter tubes in the leg vein at t=30, 15 and 0 before administration of calcitonin and at 5, 10, 20, 30, 40, 50, 60 and every 15 minutes thereafter for 2 hours. Samples of blood were centrifuged for 10 minutes at 2600 g and the resulting plasma supernatant was stored at −20° C. The concentration of calcitonin in plasma was determined by a competitive radioimmunoassay. The absolute bioavailability (i.e. relative to an intravenous dose of calcitonin) was calculated from the areas under the curve obtained from plots of the plasma concentration as a function of time obtained.

Results and Discussion:

The absolute bioavailability of calcitonin administered in water (I) was 0.015%. In the presence of 192 mg citric acid (II) the bioavailability of calcitonin increased 25 fold. The inclusion of 20 mg taurodeoxycholic acid in the formulation (III) produced an additional 2.2 fold increased in absolute bioavailability to 0.81%. The combination of a pH-lowering compound, citric acid, and an enhancer, taurodeoxycholic acid, resulted in overall 54-fold increase in the absolute bioavailability of salmon calcitonin.

TABLE 6

Effect of Citric Acid and Lauroylcarnitine on the bioavailability
of Vasopressin, Calcitonin and Insulin In Rats

| Peptide | Formulation | Peak Plasma Peptide ng/ml | Absolute Bioavailability Percent |
|---|---|---|---|
| [Arg$^8$]-Vasopressin | Vasopressin (1 mg) | 0.62 | 0.38 |
| | Vasopressin (0.1 mg) Citric Acid (48 mg) Lauroylcarnitine (5 mg) | 24.3 | 8.10 |
| Salmon Calcitonin | Calcitonin (1 mg) | 9.44 | 0.096 |
| | Calcitonin (0.1 mg) Citric Acid (48 mg) Lauroylcarnitine (5 mg) | 27.72 | 4.81 |
| Human Insulin | Insulin (1 mg) Citric Acid (48 mg) | 0.56 | 0.07 |
| | Insulin (1 mg) Citric Acid (48 mg) Lauroylcarnitine (5 mg) | 18.3 | 0.76 |

Method:

Formulations consisting of either [Arg$^8$]-vasopressin, recombinant salmon calcitonin or human insulin and the indicated additives in a total volume of 0.5 ml were administered into the duodenums of anesthetized rats as described in the legend to Table 1. Samples of blood were removed at various times and analyzed for the indicated peptide as described previously.

Results and Discussion:

In the absence of any additives the absolute bioavailability of intraduodenally administered [arg.sup.8]-vasopressin was 0.38%. When citric acid and lauroylcarnitine were added to the formulation the bioavailability of vasopressin increased to 8.1%. The bioavailability of calcitonin in the absence of an acid and an enhancer was 0.096%, which was lower than that for unformulated vasopressin. However, when citric acid and lauroylcarnitine were included in the formulation, the absolute bioavailability increased 50 fold to 4.53%. In the absence of citric acid, human insulin could not even be dissolved in water. In the presence of citric acid all of the peptide was easily dissolved, and the absolute bioavailability of intraduodenally administered human insulin was 0.07%. The absolute bioavailability of insulin increased 10 fold when lauroylcarnitine was included in the formulation. These results indicate the bioavailability of unformulated peptides was at most 0.38% and that the inclusion of an organic acid, such as citric acid, and an enhancer, such as lauroylcarnitine, increased peptide bioavailability to as much as 8.1%

TABLE 7

Effect of Enteric Coating on Absorption of sCT from Capsules in Dogs:

| Enteric Coat | Citric acid (mg) | Lauroyl-Carnitine (mg) | sCT (mg) | $C_{max}$* (pg/ml ± sem) | $T_{max}$** (min ± sem) |
|---|---|---|---|---|---|
| Yes | 632 | 65 | 12.84 | 15763 ± 4196 | 98 ± 13 |
| No | 643 | 66 | 13.07 | 3295 ± 823 | 28 ± 4 |

*Maximum plasma concentration sCT corrected to 1 mg dose.
**Time when maximum plasma sCT concentration detected.

Size 00 UPMC (hydroxypropylmethyl cellulose) capsules were each filled with a powdered blend consisting of citric acid, lauroylcarnitine, and salmon calcitonin (sCT). Half the capsules were coated with an enteric coating solution of EUDRAGIT L30D-55 (a methacrylic acid co-polymer with methacrylic acid methyl ester, an enteric coating available from ROUM Tech Inc., Maidan, Mass.), and the remaining capsules were not enteric coated. The coating process corresponded to that taught in U.S. Pat. No. 6,086,918 at col. 11, line 50 to col. 12, line 11. The average capsule content for the enteric coated and non-enteric coated capsules are shown in the table. Eight fasted dogs were each orally administered 1 uncoated capsule and 2 weeks later they were each orally administered an enteric-coated capsule. After administration of each capsule, samples of blood were taken at 15 minute intervals from an indwelling catheter for up to 4 hours. The blood samples were centrifuged and the resulting plasma supernatants were stored frozen at −20° C. The plasma samples were subsequently analyzed for sCT by a direct ELISA. The results summarized in the table as the maximum plasma sCT concentration normalized to a 1 mg dose indicates that sCT was detected in dogs orally administered enteric coated as well as uncoated capsules. Nearly three times as much sCT was detected in the plasma of dogs given enteric-coated capsules than non-coated capsules. The maximum concentration of sCT in dogs orally administered uncoated capsules was seen within 30 minutes after their administration. The maximum concentration of sCT in dogs given enteric-coated capsules was seen 98 minutes after their administration. These results demonstrate that a therapeutically effective amount of sCT can be absorbed from capsules that are not enteric-coated, and in a much faster time frame, while the amount of sCT detected in the blood is less than that seen from enteric-coated capsules. The increased speed can be advantageous, especially in the case of peptides wherein speed is more important than overall bioavailability (e.g., pain relievers). There can also be an advantage in production efficiency when the enteric coating step is not required.

TABLE 8

Effect of Formulation on Absorption of sCT from non-enteric Coated Capsules in Dogs:

| Citric acid (mg) | Lauroyl-Carnitine (mg) | Sucrose (mg) | sCT (mg) | $C_{max}$* (pg/ml ± sem) | $T_{max}$** (min ± sem) |
|---|---|---|---|---|---|
| 679 | 67 | 0 | 5.37 | 5430 ± 3203 | 26 ± 2.8 |
| 824 | 0 | 0 | 5.31 | 4612 ± 2766 | 24 ± 3.9 |
| 0 | 70 | 712 | 6.17 | 1020 ± 570 | 41 ± 9.3 |
| 0 | 0 | 805 | 5.31 | 18 ± 12 | 225*** |

*Maximum plasma concentration sCT corrected to 1 mg dose.
**Time when maximum plasma sCT concentration detected.
***sCT was only detected in 1 of 8 dogs.

Size 00 UPMC (hydroxypropylmethyl cellulose) capsules were each filled with a powdered blend consisting of the indicated amount of citric acid, lauroylcarnitine, sucrose and salmon calcitonin (sCT). The average capsule content for the capsules are shown in the table. Each week eight fasted dogs were each orally administered 1 of the uncoated capsules. After administration of the capsule, samples of blood were taken at 15 minute intervals from an indwelling catheter for up to 4 hours. The blood samples were centrifuged and the resulting plasma supernatants were stored frozen at −20° C. The plasma samples were subsequently analyzed for sCT by a direct ELISA. The results summarized in the table as the maximum plasma sCT concentration normalized to a 1 mg dose indicates that the highest concentration of sCT was detected in dogs orally administered uncoated capsules that contained citric acid. In the absence of citric acid but in the presence of lauroylcarnitine the maximum concentration of sCT in the plasma of dogs decreased by 80%. In the absence of citric acid and lauroylcarnitine, the maximum concentration of sCT in dogs decreased by 99%. These results indicate the importance of both an acid and an absorption enhancer.

TABLE 9

Absorption of non-sCT Peptides from non-Enteric Coated Capsules in Dogs:

| Peptide | Dose Mg | $C_{max}$* (pg/ml ± sem) | $T_{max}$** (min ± sem) |
|---|---|---|---|
| Dmt-DALDA | 2.40 | 7484 ± 1486 | 28 ± 4 |
| PTH (1–31) NH2 | 15.8 | 240 ± 78 | 15 |
| Insulin | 6.98 | 460 ± 95 | 15 |

*Maximum plasma concentration sCT corrected to 1 mg dose.
**Time when maximum plasma sCT concentration detected.

Size 00 UPMC capsules were each filled with a powdered blend consisting of at least 500 mg citric acid, 50 mg lauroylcarnitine and 1 of the indicated peptides. Each week eight fasted dogs were orally administered 1 of the uncoated capsules. After administration of the capsule, samples of blood were taken at 15 minute intervals from an indwelling catheter for up to 4 hours. The blood samples were centrifuged and the resulting plasma supernatants were stored frozen at −20° C. The plasma samples were subsequently analyzed for Dmt-DALDA, PTH(1-31)NH$_2$ or insulin, respectively The results summarized in the table indicate that all 3 peptides could be detected in dog plasma at sufficient concentrations to permit therapeutic use. However, the maximum concentration of peptide detected appears to be size, sequence and/or structure dependent.

Although the present invention has been described in relation to particular embodiments thereof, many other variations and modifications and other uses will become apparent to those skilled in the art. The present invention therefore is not limited by the specific disclosure herein, but only by the claims.

What is claimed is:

1. A finished pharmaceutical product adapted for oral delivery of a physiologically active peptide agent to a subject, said product in the form of a dry blend comprising:
    (a) a therapeutically effective amount of said active peptide;
    (b) at least one pharmaceutically acceptable pH-lowering agent, wherein the at least one pH-lowering agent is only selected from a tricarboxylic organic acid; and
    (c) at least one absorption enhancer effective to promote bioavailability of said active agent, wherein at least one absorption enhancer is selected from an acylcarnitine, wherein the pH-lowering agent is present in said finished pharmaceutical product in a quantity which, if said product were added to 10 milliliters of 0.1M aqueous sodium bicarbonate solution, would be sufficient to lower the pH of said solution to no higher than 5.5, and wherein the product has an outer surface, wherein the entire outer surface is free of an acid-resistant protective vehicle, said outer surface thereby being directly exposed to the aqueous environment of the stomach following administration of the product to the subject.

2. The finished pharmaceutical product of claim 1, wherein said pH-lowering compound is present in a quantity which, if said product were added to 10 milliliters of 0.1M sodium bicarbonate solution, would be sufficient to lower the pH of said solution to no higher than 3.5.

3. The finished pharmaceutical product of claim 1, wherein at least one pH-lowering agent has a solubility in water of at least 30 grams per 100 milliliters of water at room temperature.

4. The finished pharmaceutical product of claim 1, wherein said product comprises granules containing a pharmaceutical binder and, uniformly dispersed in said binder, said pH-lowering agent, said absorption enhancer and said peptide active agent.

5. The finished pharmaceutical product of claim 1, wherein the pH-lowering agent is citric acid.

6. The finished pharmaceutical product of claim 1, wherein the pH-lowering agent is present in an amount not less than 300 milligrams.

7. The finished pharmaceutical product of claim 1, wherein said peptide agent is selected from the group consisting of calcitonins and parathyroid hormones.

8. The finished pharmaceutical product of claim 1, wherein said peptide agent is selected from the group consisting of vasopressin, insulin and DALDA derivatives.

9. The finished pharmaceutical product of claim 8, wherein said peptide is DMT-DALDA.

10. The finished pharmaceutical product of claim 1, wherein the acylcarnitine is lauroyl carnitine.

11. The finished pharmaceutical product of claim 1, wherein a weight ratio of the tricarboxylic organic acid to active peptide exceeds 200:1.

12. A finished pharmaceutical product adapted for oral delivery of a physiologically active peptide agent to a subject, said product in the form of a dry blend consisting of:

a therapeutically effective amount of said active peptide;

an amount of citric acid which, when released into the intestine of the subject, is sufficient to lower the local intestinal pH substantially below the pH optima for proteases found in the intestine; and lauroyl carnitine, wherein a weight ratio of citric acid to active peptide exceeds 200:1, wherein a weight ratio of citric acid to lauroyl carnitine is between 3:1 and 20:1, and wherein the product has an outer surface, wherein the entire outer surface is free of an acid-resistant protective vehicle, said outer surface thereby being directly exposed to the aqueous environment of the stomach following administration of the product to the subject.

13. The finished pharmaceutical product of claim 12, wherein said peptide agent is selected from the group consisting of calcitonins, parathyroid hormones, vasopressin, insulin and DALDA derivatives.

\* \* \* \* \*